United States Patent
He

[19]

[11] Patent Number: 6,014,582
[45] Date of Patent: Jan. 11, 2000

[54] METHOD AND APPARATUS OF BIOSIGNAL SPATIAL ANALYSIS

[76] Inventor: Bin He, 121 Franklin Ave., River Forest, Ill. 60305

[21] Appl. No.: 08/955,683

[22] Filed: Oct. 22, 1997

Related U.S. Application Data

[60] Provisional application No. 60/029,004, Oct. 23, 1996.

[51] Int. Cl.[7] .................................................. A61B 5/00
[52] U.S. Cl. ........................................ 600/544; 600/509
[58] Field of Search ................................... 600/544, 545, 600/509

[56] References Cited

U.S. PATENT DOCUMENTS

| | | |
|---|---|---|
| 4,416,288 | 11/1983 | Freeman .................................. 600/544 |
| 5,119,816 | 6/1992 | Gevins .................................... 600/383 |
| 5,146,926 | 9/1992 | M.I.T. . |
| 5,331,970 | 7/1994 | Sam Technology, Inc. . |

OTHER PUBLICATIONS

B. He et al: "Body Surface Laplacian ECG Mapping," 1992, 1179–1191, IEEE Trans Biomed. Eng.

R. Srebro et al: "Estimating Regional Brain Activity from Evoked Potential Fields on the Scalp," 1993, 509–516, IEEE Trans. Biomed. Eng.

P.L. Nunez et al: "A theoretical and experimental study of high resolution EEG based on surface Laplacians and cortical imaging," 1994, 40–57, Electroenecepha. Clin. Neurophsiology.

A. Gevins: "High resolution EEG: 124–channel recording, spatial deblurring and MRI integration methods," 1994, 337–358, Electroencepha. Clin. Neurophysiology.

B. He et al: "Cortical Source Imaging from Scalp Electroencephalograms," 1996, 257–258, Medical & Biological Eng. & Comput., vol. 34, Suppl. 1, Part2.

F. Babiloni et al: "High resolution EEG: a new model–dependent spatial deblurring method using a realistically–shaped MR–constructed subject's head model," 1997, 69–80, Electroencepha. Clin. Neurophysiology.

B. He: "Principles and Applications of Laplacian Electrocardiogram," 1997, 133–138, IEEE Engineering in Medicine and Biology.

T.F. Oostendorp et al: "The surface Laplacian of the potential: Theory and Applications," 1996, 394–405, IEEE Trans. Biomed. Eng.

*Primary Examiner*—Robert L. Nasser

[57] ABSTRACT

An instrument and method for measuring, analyzing and visualizing electrical activities in a biological system, comprising a plurality of sensors for detecting signals over a part of a surface of the biological system, a data acquisition unit for collecting the signals and for time-domain pre-processing, a positioning device for determining positions of the sensors, an estimator for determining surface differentials of the collected signals, a spatial pre-filter for reducing measurement noise in the collected signals, a spatial threshold filter for reducing volume conduction distortion, and a unit for displaying the processed signals in one of the time domain and space domain, together with the collected signals and the surface differentials of the collected signals. The collected biosignals over the scalp are also deconvolved to estimate the electrical activity over the brain surface.

16 Claims, 7 Drawing Sheets

METHOD AND APPARATUS OF BIOSIGNAL SPATIAL ANALYSIS

This patent application is based on previous provisional patent applications 60/029,004 "Methods and Apparatus of Biological Analysis Using High Resolution Spatial Filters," filed on Oct. 23, 1996, and "Methods and Apparatus of Biosignal Spatial Analysis," filed on Sep. 12, 1997.

FIELD OF THE INVENTION

This invention relates to instruments and methods for analysis of biosignals associated with biological and physiological processes in a biological system.

BACKGROUND OF THE INVENTION

Information concerning the electrical activities of the organ systems is widely used to assess the health characteristics of both people and animals. For example, analysis of the morphology of the waveforms of the electrocardiogram provides an indication of the current status of cardiac electrical activity. The standard clinical method of determining cardiac electrical activity is the 12-lead electrocardiograms or vectorcardiograms, which are obtained by placing a few electrodes on the limbs and chest to record the time courses of the electrical potential on these electrodes. Similarly, 10–20 electroencephalograms are widely used in the clinical setting to help diagnose brain abnormalities.

Recently, techniques have been introduced in order to provide the spatial information on bioelectrical activities by mapping the electrical potential over a large area of the body surface. These methods, in general, use a large number of electrodes placed over a large area over the body surface, thereby providing a high spatial sampling over the space domain. Unfortunately, it has been shown that the direct display of a complete set of distribution of bioelectrical potentials over the body surface still does not provide spatial details on the underlying bioelectrical activities, because of distortion introduced by the body volume conductor.

Another class of instrumentation is available for the specific purpose of determining origins of electrophysiological or pathophysiological events using electrical methods. This technology also uses electrodes, but placing them directly close to or on the surface of the organs. Therefore this technology is invasive. Although these methods provide much higher spatial details in determining origins of bioelectrical activities, the invasive nature of this technology limits the application to human beings.

Thus, there is a great need for non-invasive analytical instruments and methods that would provide important spatial information regarding the bioelectrical activities.

Attempts have been made to process the recorded body surface potentials or to correct the volume conduction distortion by incorporating the properties of passive body conductor. The surface Laplacian over the body surface has been used to improve the spatial resolution of bioelectrical signal analysis. It has been shown that the surface Laplacian distribution facilities the analysis and interpretation of biosignals. He and Cohen introduced a technique to measure and visualize the body surface Laplacian using a set of bipolar electrodes, which was published in IEEE Transactions on Biomedical Engineering, vol. 39, 1179, 1992. See also U.S. Pat. No. 5,146,926. Oostendorp and van Oosterom gave a numerical algorithm on evaluating the surface Laplacian from assumed bioelectrical sources, see "The surface Laplacian of the potential: Theory and applications," IEEE Trans. On Biomedical Engineering, vol. 43, 394, 1996. An approach has also been described by He to estimate the body surface Laplacian electrograms from potentials, see "Principles and Applications of the Laplacian Electrocardiogram," IEEE Engineering in Medicine and Biology, 133, 1997. Nunez et al. studied the surface Laplacian on the scalp using a spline algorithm, see "A theoretical and experimental study of high resolution EEG based on surface Laplacian and cortical imaging", Electroenceph. and Clin. Neurophysiol. 90, 40, 1994. Gevins et al. described a method of estimating surface Laplacian in a realistically shaped head model from scalp potentials, see U.S. Pat. No. 5,331,970. In these approaches, the surface Laplacian of the potential was measured or estimated from potential data using a local or global estimation schemes. However, in the prior art, no descriptions have been given on using the spatial pre-filtering before the estimation of the surface Laplacian of the potential. No descriptions have been given to conduct spatial threshold filtering using both potential and the surface differentials of the potential in spatial analysis of bioelectrical activity.

Attempts have also been made to reduce the volume conduction distortion by estimating the bioelectrical potentials over the brain surface from body surface potentials. Srebro et al. linked the evoked potential field on the scalp with brain surface field by assuming the head being homogeneous, see "Estimating regional brain activity from evoked potential field on the scalp", published by R. Srebro et al. in IEEE Trans. Biomed. Eng. 40, 509, 1993. Regularized inversion is applied to obtain the brain surface potential estimation. However, the lack of the significant inhomogeneity (the skull) in their head model results in considerable numerical errors. He et al. proposed an improved version of cortical imaging algorithm by incorporating a 3-spheres inhomogeneous head model and a closed spherical dipole layer of up to 1000 dipoles. See "Cortical source imaging from scalp electroencephalograms", published in Med. Biol. Eng. Comput. Vol. 34, 257, 1996. Recently, Babiloni et al. further extended the cortical imaging algorithm to a realistically shaped inhomogeneous head model with 364 dipoles. The boundary element technique was used to evaluate the potential field in the realistically shaped head model in Babiloni's algorithm, although the brain sources are still assumed to consist of 364 dipoles inside the brain. See "High resolution EEG: a new model-dependent spatial deblurring method using a realistically-shaped MR-constructed subject's head model", published by F. Babiloni et al. in Electroencephalography and clinical Neurophysiology, vol. 102, 69, 1997. Gevins et al. reported a cortical imaging technique in a realistically shaped inhomogeneous head model using finite element method, see "High Resolution EEG: 124-channel recording, spatial deblurring and MRI integration methods," published in Electroenceph. clin. Neurophy., vol. 90, 337, 1994. See also U.S. Pat. No. 5,331,970. In this method, Poisson's equation is applied to a conducting volume between scalp and cortical surface, and the finite element method is used to handle the complex geometry and varying conductivity of the head. However, the finite element method based technique has intrinsic limitations because it requires detailed three-dimension information on the tissue conductivity, which has only been known approximately up to date. The need to create and manipulate a large amount of three-dimension information requires significant storage and computation capability. Furthermore, the reported finite element method inverse reconstruction procedure necessitates the solution of a nonlinear problem. Therefore, there is a great need to further improve brain electric imaging technique.

SUMMARY OF THE INVENTION

While the present invention is described with respect to biological systems, it can be understood that the teachings apply to nonbiological systems as well, in which activities can be analyzed from measurements made at a surface.

In accordance with the present invention, a signal analysis instrument for measuring, analyzing and visualizing biosignals comprises means for collecting biosignals over a part of a surface inside or outside of the body of a subject, means for determining positions of the sensors, means for reducing noise in the collected biosignals, means for reducing volume conduction distortion using a spatial threshold filter using both biosignals and the surface differentials of the biosignals, and means for displaying the processed biosignals.

In accordance with one aspect of the present invention, a signal analysis instrument for measuring, analyzing and visualizing brain electrical signals comprises means for collecting bioelectrical potentials over a part of a scalp of a subject, means for determining positions of the recording electrodes over the scalp, means for reducing measurement noise in the collected scalp potentials, means for reducing volume conduction distortion and for comprising a high-resolution image of the brain bioelectrical activity by a spatial threshold filter using both the electrical potentials and the surface differentials of the potentials, and means for displaying the processed signals of the subject.

This aspect of the invention further relates to methods wherein scalp electroencephalographic potentials are measured using electrodes with the electrode positions being determined, passed through a spatial pre-filter for reducing measurement noise, and the source signals of brain electrical activity are estimated using a spatial threshold filter in which both the scalp potentials and its surface differentials are used.

This aspect of the invention further relates to methods wherein body surface electrocardiographic potentials are measured using electrodes, and the electrode positions are determined, and passed through a spatial pre-filter for reducing measurement noise. The source signals of cardiac electrical activity are estimated using a spatial threshold filter in which both the body surface potentials and its spatial differentials are used.

This aspect of the invention also relates to means and methods for guiding catheter ablation of a part of the heart or other electrically active organs. This invention can be utilized to help identify the ablation site, for example, in order to prevent ventricular tachycardia. In accordance with this aspect of the invention, biosignals are collected by a catheter, simultaneously or sequentially, the signals are then pre-processed to filter out measurement noise, and the source signals of cardiac electrical activity are estimated using a spatial threshold filter in which both the biosignals collected by a catheter and its spatial differentials are used.

In accordance with another aspect of the present invention, a signal analysis for measuring, analyzing and visualizing biomagnetic signals comprises means for collecting biomagnetic signals over a part of a surface outside of the body of a subject, means for determining positions of the biomagnetic sensors, means for reducing measurement noise in the collected biomagnetic signals, means for estimating the source signals by a spatial threshold filter in which both the measured biomagnetic signals and its spatial differentials are used, and means for displaying the processed biomagnetic signals.

This aspect of the invention also relates to means and methods for signal analysis of both bioelectrical and biomagnetic signals collected by multi-electromagnetic sensors. The collected bioelectromagnetic signals are pre-processed to filter out measurement noise, and the source signals are estimated by a spatial threshold filter using both the measured electromagnetic signals and its spatial differentials. The estimated source signal distributions, bioelectromagnetic signals as well as their spatial differentials are then displayed.

In accordance with the present invention, the spatial differential of the signal can be a two-dimensional Laplacian (surface Laplacian) of the signal, a surface Laplacian of the surface Laplacian of the signal, and can also be a spatial differential with an order of 2, 4, 6, or higher order.

In accordance with a further aspect of the present invention, a signal analysis instrument for measuring, analyzing and visualizing brain electrical activity comprises means for collecting bioelectrical potentials over a part of a scalp of a subject, means for determining positions of the recording electrodes over the scalp, means for obtaining information regarding geometry and conductivity distribution of the head of the subject, means for reducing measurement noise in the collected scalp potentials, means for reducing volume conduction distortion by estimating the cortical electrical signals from the scalp electrical potentials using a boundary element technique, and means for displaying the processed signals of the subject.

The present invention provides a new method of reducing measurement noise and volume conduction distortion associated with bioelectromagnetic signals, thus enhancing significantly our capability in assessing and localizing origins of biological signals. This feature of the present invention may enable it to become an important clinical diagnostic tool guiding clinical diagnosis and management of brain and cardiac disorders.

DETAILED DESCRIPTION OF THE INVENTION

Figure 1:
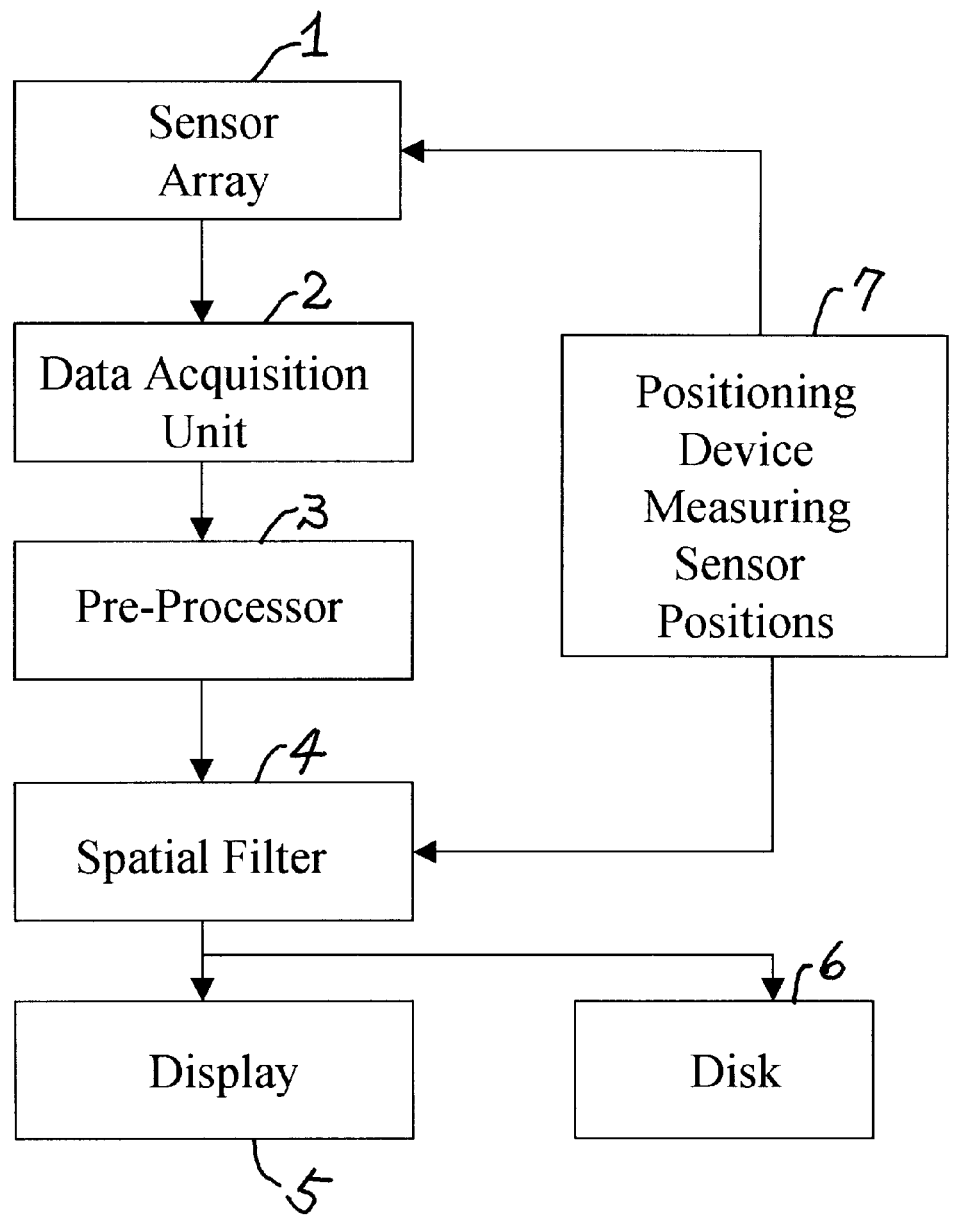
FIG. 1 is a schematic diagram of a biosignal analysis instrument in accordance with the present invention.

Since the electrical signals are measured at remote positions over the body surface from their biological origins, they are essentially summed responses from a number of active biological cells inside the body. The method of the present invention invokes two ways to improve the resolution of spatial information obtained by electrical recordings. The first one is to use the counter-filtering characteristics of surface differentials of the potential with combining using the electrical potential with surface differentials of the potential. The second one is to use a spatial deconvolution for reconstructing brain electrical activity over the brain surface from the scalp potential recordings in a realistically shaped inhomogeneous head model using the boundary element technique.

The spatial filtering comprises pre-filtering of measurement noise, estimation of surface differentials of the bio-electrical signal, and spatial threshold filtering of biosignals using both the biosignals and the surface differentials of the biosignals.

In accordance with the present invention, a spatial pre-filtering of measurement noise in the collected biosignals is utilized. The biosignals collected by a plurality of sensors are first pre-set to a zero-activity level, which is defined as the average signal value over a selected period during which the organ system being studied is considered as being electrically silent. The biosignals are then passed through a band-pass time-domain filter to remove noise from the biosignals. The processed biosignals are further processed in the space domain using the following procedures if the biosignals are recorded over a N1 by N2 array of sensors on a surface. When the sensors are not located on a regular lattice, the signals over the N1 by N2 array can be obtained by interpolation from the measured signals. A mean value $\mu$ and variance $\sigma^2$ of the biosignals around each location (i, j) of the sensor array in the space domain are estimated, where i=1, 2, ..., N1 and j=1, 2, ..., N2. Then the biosignals are processed according to the following equation:

$$S(i, j) = \mu + \frac{\sigma^2 - v^2}{\sigma^2}[F(i, j) - \mu] \quad (1)$$

where S, F represent the processed and before-processed biosignals at a location (i, j) in the space domain, and $v^2$ is the variance of noise. The variance of noise can be estimated from the average of local biosignal variance over all the neighboring locations.

In accordance with a preferred embodiment, the invention uses a spatial threshold filter to estimate the source signals by applying the threshold filtering as follows:

$$h(I)=S(I)*L(I) \quad (2)$$

where h(I), S(I), and L(I) refer to the estimated source signal, the pre-processed signal, and the surface Laplacian of the pre-processed signal. I refers to a position where the signal is collected or interpolated from collected signals. In some cases, the following equation can be used, $$h(I)=|S(I)|*L(I) \quad (3)$$

Similarly, a series of the above threshold filter can be applied as follows, $$h(I)=S(I)*L(I)*LL(I)* \ldots (4)$$

where LL(I) refers to the surface Laplacian of the surface Laplacian of the recorded signal. The pre-processing scheme described above in equation (1) can be appropriately applied to some signals in equation (4). In equation (4), "..." refers to continuous operation of multiplication of the processed signals and their spatial differentials. "*" refers to multiplication operation in the space domain at each location. Such locations can be the positions of recording electrodes, or those locations where the signals are interpolated from recorded biosignals.

FIG. 1 illustrates one application of the present invention. Signals are sensed by a sensor array 1 and passed to a data acquisition unit 2, where the signals are amplified, band-pass filtered, A/D converted, and then are passed to a pre-processor 3, where the signals are further processed in digital form including zero-activity level adjustment and further timedomain filtering. The positions of the sensors 1 may be determined in advance based on the design of the sensor array 1, or may be measured by a positioning device 7. The unit 2 can be a dedicated hardware performing all necessary functions as to obtain analyzable signals. The unit 2 can also be a combination of several functional blocks. The signals and/or the sensor position data are then passed to a spatial filter 4, which is an essential part for removing noise and for correcting distortion. The spatial filter 4 comprises two functions: spatial pre-filtering and spatial threshold filtering, where the operations of these filters are defined by the equations (1)–(4) and by FIG. 2. The signals may be processed only by the spatial pre-filter or by the spatial threshold filter, or by a combination of these filters. The processed signals are then sent to a display unit 5 for displaying, and/or sent to a disk 6 for permanent storage.

Figure 2:
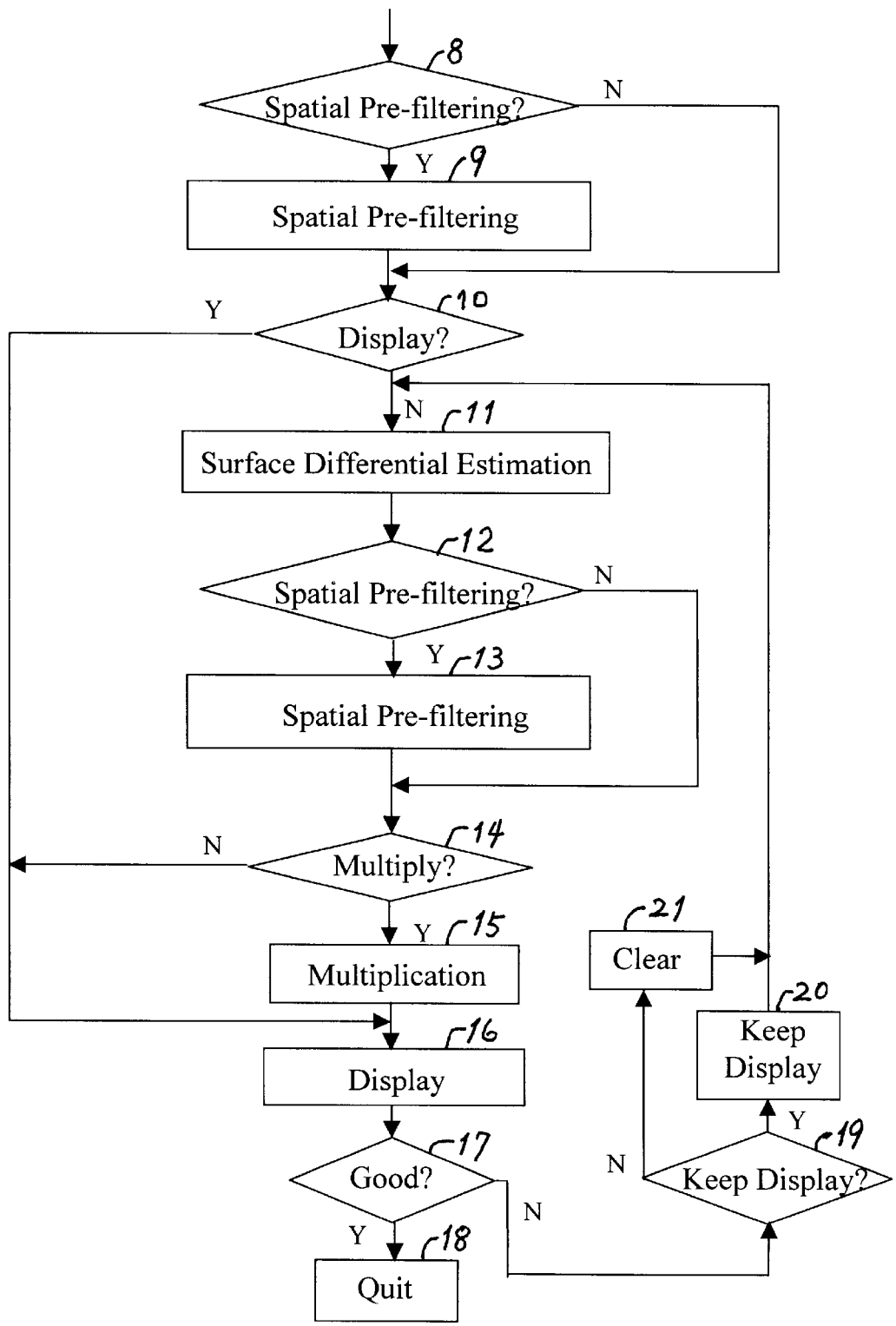
FIG. 2 illustrates the operation flowchart of the spatial filter in accordance with the present invention.

FIG. 2 illustrates the operation flowchart of the spatial filter. The signals sensed by the sensor array, which has been pre-processed, and the sensor position data are passed for determination of spatial pre-filtering at Step 8. If a decision is made to perform the spatial pre-filtering, the signals are passed for the spatial pre-filtering at Step 9, otherwise, to Step 10. At Step 10, a decision is made whether to display the signals. If yes, the signals are sent to the display unit 5, at passed to Step 16, for displaying. If no, the signals are passed to Step 11 for surface differential estimation of the signal, preferably to estimate the surface Laplacian of the signals. The next step 12 is to decide if to perform spatial pre-filtering on the output signals from Step 11. If yes, the output signals are passed for spatial pre-filtering at Step 13. If not, the output signals of Step 11 are passed for determination of multiplication at Step 14, where whether the multiplication of the signal with its surface differentials is decided. If yes, the multiplication will be performed point by point in the space domain. If not, the surface differential of the signals is passed for displaying at Step 16. When the signals and/or its surface differentials are displayed at Step 16, a decision is made at Step 17 as to whether the results are good enough. If yes, the signals and estimated surface differentials are sent out at Step 18 and the operation quits. If not, at Step 19, whether the display should be kept will be decided. If yes, the display will be kept at Step 20, if not, at Step 21, the display will be cleared. The output of Step 20 or 21 is sent back to Step 11 for further estimation of the surface differential of the output of Step 12 or 13. The iterative operation starts again. Every time, the original signal (whether pre-filtered or not) will be multiplied, as well as its surface differential, its surface differential of the surface differential ... and so on. This operation is defined in equation (4).

Figure 3:
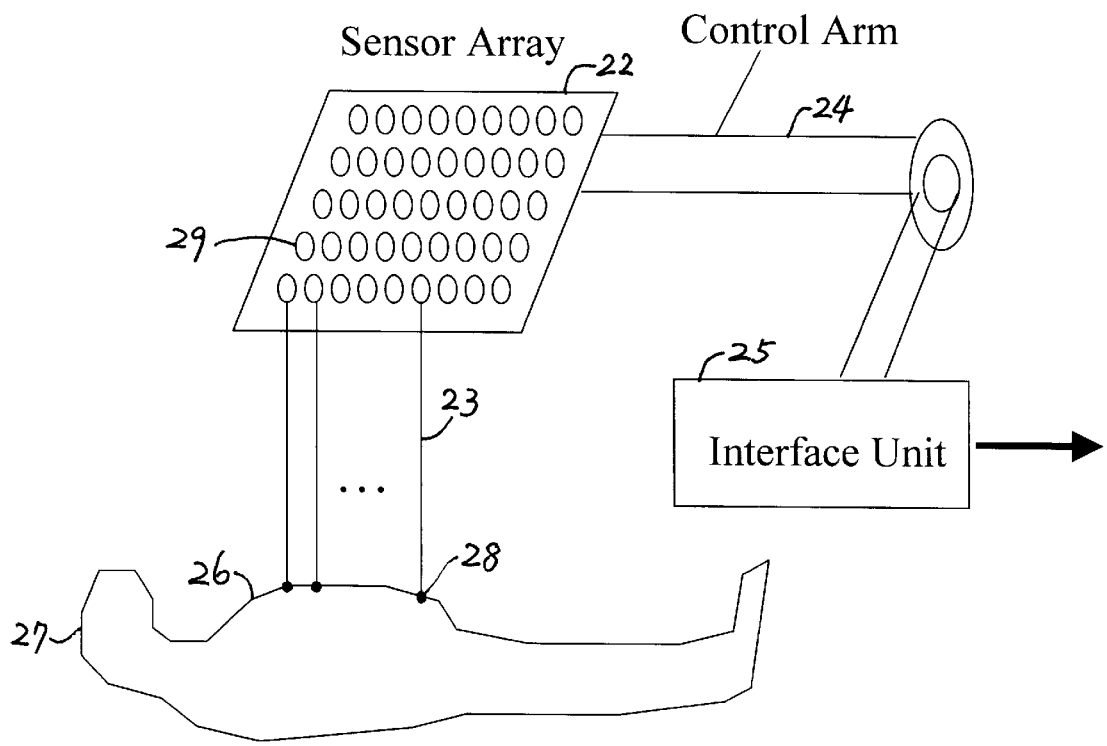
FIG. 3 illustrates a preferred embodiment of application of the present invention.

In another embodiment of the present invention, an electromechanical sensor array is used to obtain the body surface potentials and sensor-position information. Such a schematic illustration is shown in FIG. 3. A plate 22 composed of N1 by N2 sensors 23 is attached to a mechanical control arm 24. The control arm 24 controls the mechanical position of the sensor plate 22 and passes biopotentials and sensor position data to an interface unit 25. The interface unit 25 further passes data to the data acquisition unit 2 in FIG. 1. The sensors 23 have the same length and are capable of sliding down after the plate 22 is adjusted to an appropriate position using the control arm 24. The down tip 28 of each sensor includes a disk-shaped conductor, which serves as an electrode to sense the biopotential on the body surface. The plate 22 has certain depth so that the contacting holes 29 in the plate 22 are capable of passing the sensed potentials and the information on the length of the sensor 23 to the interface unit 25 through the control arm 24. The position information on the electrode sensor tips 28 are determined by the structure of the plate 22 and sensors 23 and the length of each sensor 23. The sensors 23 can be placed on a part of the chest 26 of a subject lying down on an examining bed for analyzing cardiac electrical activity of the subject. The sensors 23 can also be placed on a part of the scalp 27 of a subject for analyzing brain electrical activity of the subject.

Figure 4:
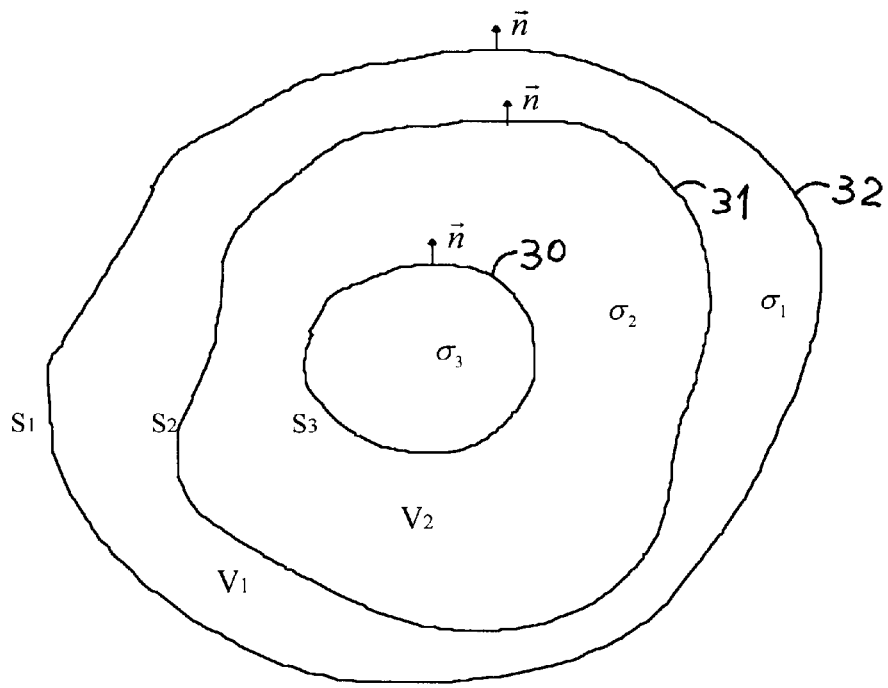
FIG. 4 illustrates a schematic diagram of a three-shell conductor, which represents the head volume conductor.

In accordance with the second way of the present invention, the boundary elements are used to relate the scalp potentials to the cortical potentials in a multi-shell realistically shaped inhomogeneous head conductor model. FIG. 4 illustrates such a three-shell inhomogeneous head conductor with the brain surface 30, the skull surface 31, and the scalp 32. By applying the Green's second identity, the electrical potential on the scalp 32 and the skull surface 31 can be related by the following integral equation, $$u_{(\vec{r}^*)} = \frac{1}{4\pi} \int\!\!\int_{S1} u \cdot d\Omega - \frac{1}{4\pi} \int\!\!\int_{S2} u \cdot d\Omega - \frac{1}{4\pi} \int\!\!\int_{S2} \frac{1}{r} \cdot \frac{\partial u}{\partial r_n} dS \quad (5)$$

where $u_{(\vec{r}^*)}$ is the electrical potential at the observation point $\vec{r}^*$, $d\Omega$ is the solid angle of an infinitesimal surface element $dS$ as seen from $\vec{r}^*$, $\partial u/\partial r_n$ is the first derivative of the potential u with respect to the outward normal to dS 1/r, and r is the distance from the observation point $\vec{r}^*$ located within V to the surface element. By descretizing the equation (5), the following matrix equation can be obtained, $$P_{11}U_1 + P_{12}U_2 + G_{12}\Gamma_2 = 0 \quad (6)$$

where $U_k$ is the column vector consisting of potentials at every surface element on $S_k$, and $\Gamma_k$ is the column vector consisting of $\partial u/\partial r_n$ at every triangle element on $S_k$ but just inside of $V_1$. $P_{11}$, $P_{12}$ and $G_{12}$ are coefficient matrices. Similarly, taking the limit of observation point $\vec{r}^*$ approaching the surface element on $S_2$ just from the inside of $V_1$, gives the equation $$P_{21}U_1 + P_{22}U_2 + G_{22}\Gamma_2 = 0 \quad (7)$$

Applying Green's second identity to the volume $V_2$ between $S_2$ and $S_3$ and considering the boundary conditions on $S_2$: $U_2 = U_2$, $\sigma_1\Gamma_2 = \sigma_2\Gamma_2$, the following matrix equation can be obtained, $$U_1 = T_{13}U_3 \quad (8)$$

where $T_{13}$ is the transfer matrix from brain surface potentials to the head surface potentials, which is a function of the geometry and conductivity of the head. Therefore, the brain surface potential can be linearly obtained from the scalp potential and the passive properties of the head by the following equation:

$$U_3 = T^{\#}U \quad (9)$$

where $T^{\#}$ is the pseudo-inverse matrix of the matrix T. Equation (9) indicates that by taking the pseudo-inversion of T and multiplying by the scalp recordings, the brain surface potential distribution is obtained with some constraints such as minimum norm. Numerical algorithms, such as the truncated singular value decomposition algorithm or Tikhonov regularization algorithm, can be used to solve this problem.

Figure 5:
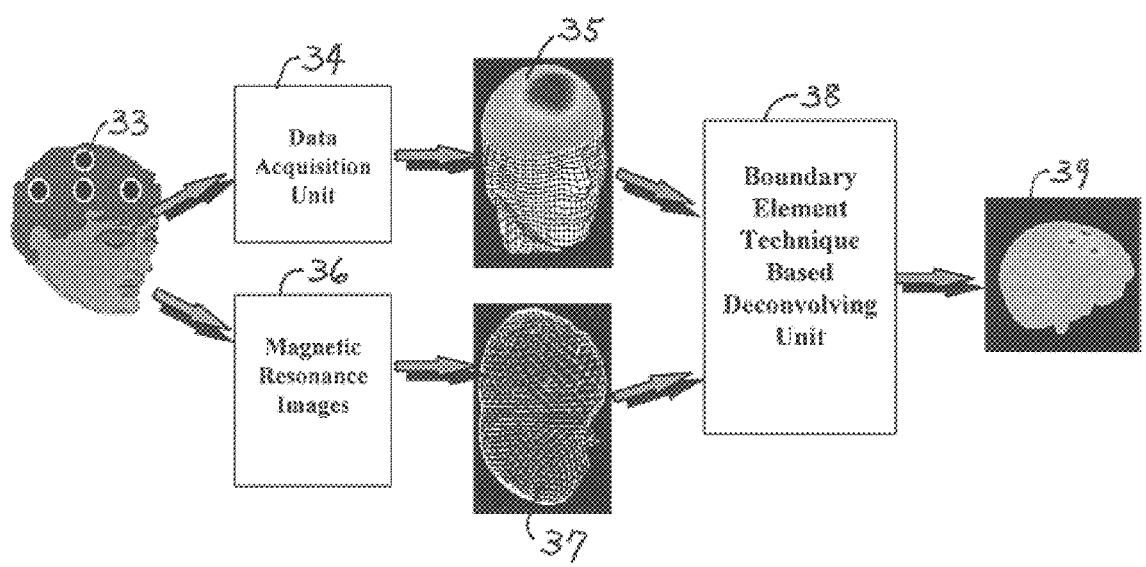
FIG. 5 illustrates another embodiment of the present invention for analyzing and visualizing brain electrical signals over the brain surface.

In accordance with another embodiment of the present invention as shown in FIG. 5, electrical potential signals are sensed by a plurality of electrodes 33 on the scalp and passed to the data acquisition unit 34, where the signals are amplified, band-pass filtered in time domain, and/or digitized. The unit 34 may also obtain the information on the geometry positions of the sensors 33. The scalp electrical signals and sensor-position data are then used to construct scalp potential distribution 35, after a pre-processing of the recorded signals to reduce measurement noise by unit 34. The geometry information on the head conductor may be obtained from magnetic resonance images 36 of the subject, and a 3-shell boundary element model 37 is constructed. Using all these information, the brain surface potential images are estimated by the deconvolving unit 38. The estimated brain surface source signals are then sent to a display unit 39 for displaying, and/or sent to a disk for storage.

EXAMPLE I

Figure 6A:
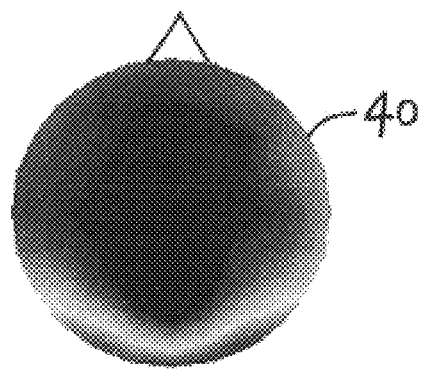
FIGS. 6(A)–(D) illustrate an example of applying the present invention in analyzing brain electrical signals.
Figure 6B:
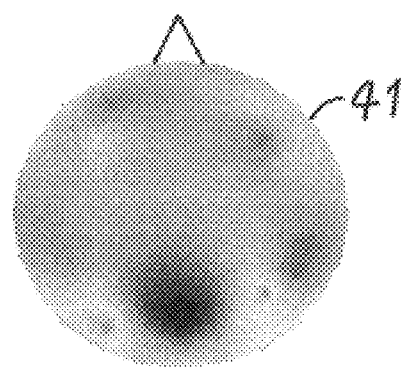
Figure 6C:
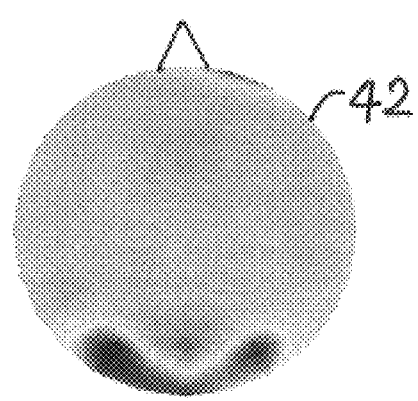
Figure 6D:
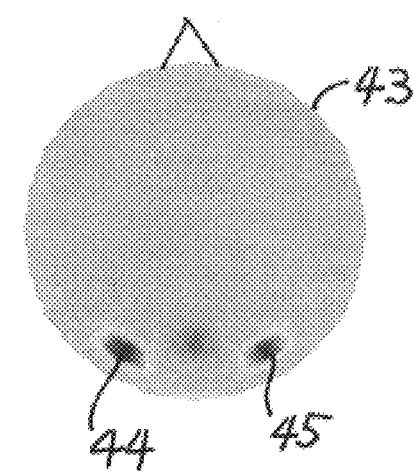

FIGS. 6(A)–6(D) illustrate an example of applying the present invention in analyzing brain electrical signals. The scalp evoked potentials were measured using 32 electrodes uniformly arranged over the scalp of a human subject. The electrical potentials were recorded when the subject was stimulated by a flash light with both eyes open. FIG. 6(A) shows an example of the scalp potential image 40 at a time after visual stimulation. FIG. 6(B) shows the spatial image of the second spatial differential (the negative surface Laplacian) 41 of the potential illustrated in FIG. 6(A). FIG. 6(C) shows the image of the fourth surface differential (surface Laplacian of the surface Laplacian) 42 of the potentials illustrated in FIG. 6(A). FIG. 6(D) shows an example of the source signal image 43 obtained after applying the present invention, which is corresponding to (potential) * (negative surface Laplacian of the potential) * (fourth differential of the potential with pre-processing of the Laplacian signal). The notion * refers to the operation of multiplication of signals at each position in space domain. FIG. 6(D) clear indicates two areas 44 and 45 of activity directly overlying the left and right visual cortex, which correspond to the brain electrical activity evoked by the flash stimulation. FIG. 6(D) shows that the source signal image obtained using the present invention demonstrates a superior performance in reducing volume conduction distortion and in localizing and analyzing brain electrical activity.

EXAMPLE II

Figure 7A:
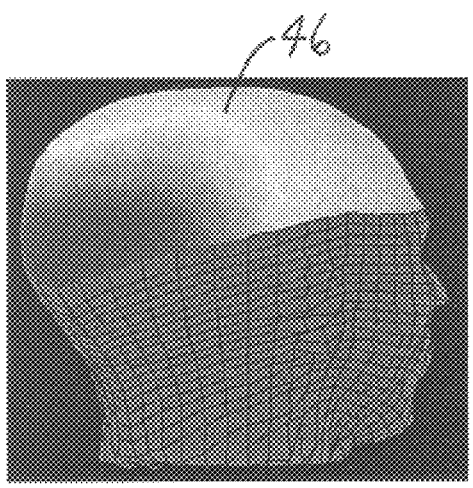
FIGS. 7(A)–(B) illustrate another example of applying the present invention in analyzing and visualizing brain electrical signals.
Figure 7B:
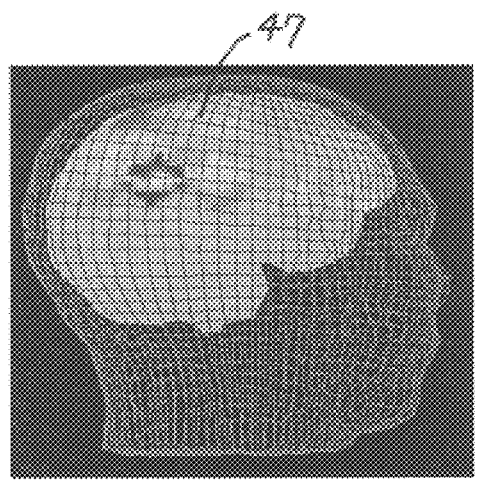

FIGS. 7(A)–(B) illustrate an another example of applying the present invention in analyzing brain electrical signals. The scalp evoked potentials were measured by using 32 electrodes uniformly arranged over the scalp of a human subject. The electrical potentials were recorded when the subject was stimulated by a flash light with left eye open. FIG. 7(A) shows an example of the scalp potential image 46 at a time after visual stimulation. FIG. 7(B) shows the analyzed image over the brain surface 47 according to the present invention. Comparing to the scalp potential image 46, the analyzed brain surface potential image 47 of the present invention provides much greater spatial details over directly the brain surface.

What is claimed is:

1. A method of measuring, analyzing and visualizing electrical activities in a system comprising the steps of:
   (a) collecting signals over a part of a surface of the system using a plurality of sensors and a data acquisition unit, (b) determining positions of the sensors, (c) reducing measurement noise in the collected signals by applying a spatial pre-filtering, (d) reducing volume conduction distortion in the collected signals by using a spatial threshold filter which uses simultaneously both the collected signals and surface differentials of the collected signals, and (e) displaying simultaneously the processed signals in one of the time domain and space domain, together with the collected signals and the surface differentials of the collected signals.

2. The method of claim 1 wherein said steps (a) to (e) are repeated for sequential time epochs.

3. The method of claims 1 wherein the system is a biological system.

4. The method of claim 1 wherein the surface is one of an external surface, an internal surface, and a surface outside of a biological system.

5. The method of claim 1 wherein the electrical activities originate in the brain.

6. The method of claim 1 wherein the electrical activities originate in the heart.

7. The method of claim 1 wherein the spatial pre-filtering is performed using the following equation:

$$S(i, j) = \mu + \frac{\sigma^2 - v^2}{\sigma^2}[F(i, j) - \mu]$$

wherein a local mean $\mu$ and variance $\sigma$ of the signals around each position (i, j) in the space domain are estimated at positions i=1, 2, ..., N1 and j=1, 2, ..., N2; S, F represent the processed and before-processed signals at a position (i, j); $v^2$ refers to the variance of noise.

8. The method of claim 1 wherein the surface differentials are the surface Laplacian and the surface Laplacian of the surface Laplacian, wherein the following threshold filtering $$h(I)=S(I)*L(I)*LL(I)$$

is performed, where h(I), S(I), L(I), and LL(I) refer to the processed signal, the collected signal, the surface Laplacian of said signal, and the surface Laplacian of the surface Laplacian of said signal, at the location I; the notion "*" refers to multiplication operation in the space domain of the signals at each position I.

9. The method of claim 1 wherein the surface differentials are the surface Laplacian and the surface Laplacian of the surface Laplacian, wherein the following threshold filtering $$h(I)=S(I)*L(I)*LL(I)$$

is performed, where h(I), S(I), L(I), and LL(I) refer to the processed signal, the collected signal, the surface Laplacian of said signal, and the surface Laplacian of the surface Laplacian of said signal, at the location I; the notion "*" refers to multiplication operation in the space domain of the signals at each position I; where the following pre-filtering is performed to S, L, and LL, $$S(i, j) = \mu + \frac{\sigma^2 - v^2}{\sigma^2}[F(i, j) - \mu]$$

wherein a local mean $\mu$ and variance $\sigma^2$ of the signals around each position (i, j) in the space domain are estimated at positions i=1, 2, ..., N1 and j=1, 2, ..., N2; S, F represent the processed and before-processed signals at a position (i, j); $v^2$ refers to the variance of noise.

10. The method of claim 1 further including a step of determining the surface Laplacian of the signals using one of a local Laplacian estimation algorithm, global Laplacian estimation algorithm, spline Laplacian estimation algorithm, and non-spline Laplacian estimation algorithm.

11. The method of claim 1 wherein the biosignals are collected by a cardiac catheter.

12. An apparatus for measuring, analyzing and visualizing electrical activities in a biological system, comprising a plurality of sensors for detecting signals over a part of a surface of the biological system, means for collecting the detected signals, means for determining positions of the sensors, means for determining surface differentials of the collected signals, means for reducing measurement noise in the collected signals by applying a spatial pre-filtering, means for reducing volume conduction distortion in the collected signals based on both the collected signals and the surface differentials in the space domain, and means for displaying the processed signals in one of the time domain and space domain, together with the collected signals and the surface differentials of the collected signals.

13. The apparatus of claim 12 further including means for analyzing the electrical activities for sequential time epochs.

14. The apparatus of claim 12 wherein the means for collecting the signals and means for determining the surface differentials of the signals include, respectively, an array of electrodes.

15. The apparatus of claim 12 wherein the plurality of sensors include an array of magnetic sensors.

16. The apparatus of claim 12 wherein the plurality of sensors includes an array of magnetic sensors and an array of electrodes.

* * * * *